United States Patent [19]

Marsico, Jr. et al.

[11] Patent Number: 4,576,957

[45] Date of Patent: Mar. 18, 1986

[54] N-(SUBSTITUTED PHENYL)-N'-[(1H-IMIDAZOL-1-YL) AND (1H-1,2,4-TRIAZOL-1-YL)ALKYL]UREAS

[75] Inventors: Joseph W. Marsico, Jr., Pearl River, N.Y.; William B. Wright, Jr., Woodcliff Lake, N.J.; Jeffery B. Press, Tuxedo, N.Y.

[73] Assignee: American Cyanamid Company, Stamford, Conn.

[21] Appl. No.: 628,095

[22] Filed: Jul. 5, 1984

[51] Int. Cl.$^4$ .................. A61K 31/41; A61K 31/415; C07D 233/61; C07D 249/08
[52] U.S. Cl. .................................... 514/383; 560/330; 514/399; 548/336; 548/341; 548/262

[58] Field of Search .............. 548/341, 262; 514/383, 514/399

[56] References Cited

U.S. PATENT DOCUMENTS

| 3,478,039 | 11/1969 | Bell | 548/341 |
| 3,892,764 | 7/1975 | Metzger et al. | 548/341 |
| 4,353,921 | 10/1982 | Diamond et al. | 548/341 |
| 4,482,558 | 11/1984 | Richardson et al. | 548/262 |
| 4,489,089 | 12/1984 | Wright et al. | 548/336 |

Primary Examiner—Alton D. Rollins
Attorney, Agent, or Firm—Edward A. Conroy, Jr.

[57] ABSTRACT

N-(Substituted phenyl)-N'-[(1H-imidazol-1-yl) and (1H-1,2,4-triazol-1-yl)alkyl]ureas which are inhibitors of thromboxane synthetase enzyme.

21 Claims, No Drawings

N-(SUBSTITUTED PHENYL)-N'-[(1H-IMIDAZOL-1-YL) AND (1H-1,2,4-TRIAZOL-1-YL)ALKYL]UREAS

SUMMARY OF THE INVENTION

This invention relates to new organic compounds and, more particularly, is concerned with novel N-(substituted phenyl)-N'-[(1H-imidazol-1-yl)alkyl]ureas and N-(substituted phenyl)-N'[(1H-1,2,4-triazol-1-yl)alkyl]ureas which may be represented by the following structural formula:

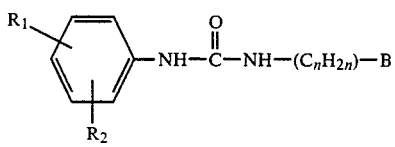

wherein $R_1$ and $R_2$ may be the same or different and are each selected from the group consisting of hydrogen, fluoro, chloro, bromo, trifluoromethyl, alkyl($C_1$–$C_3$) and alkoxy($C_1$–$C_3$); n is an integer from 2 to 8, inclusive; and B is 1H-1,2,4-triazol-1-yl or a moiety of the formula:

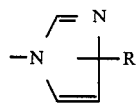

wherein R is hydrogen, alkyl($C_1$–$C_3$) or phenyl.

The organic bases of this invention form non-toxic acid-addition salts with a variety of pharmacologically acceptable organic and inorganic salt-forming reagents. Thus, acid-addition salts, formed by admixture of the organic free base with one equivalent of an acid, suitably in a neutral solvent, are formed with such acids as sulfuric, phosphoric, hydrochloric, hydrobromic, sulfamic, citric, lactic, malic, succinic, maleic, fumaric, tartaric, acetic, benzoic, gluconic, ascorbic and the like. For purpose of this invention the free bases are equivalent to their non-toxic acid-addition salts. The acid-addition salts of the organic bases of this invention are, in general, crystalline solids, relatively soluble in water, methanol and ethanol but relatively insoluble in non-polar organic solvents such as diethyl ether, benzene and toluene.

DETAILED DESCRIPTION OF THE INVENTION

The novel compounds of the present invention may be readily prepared according to the following reaction scheme wherein $R_1$, $R_2$, B and n are as described hereinabove.

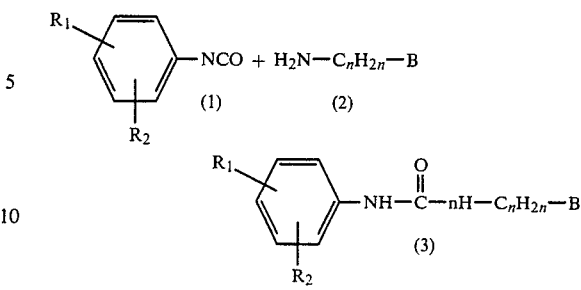

In accordance with the above reaction scheme, a 1H-1,2,4-triazole-1-alkylamine or 1H-imidazole-1-alkylamine(2) is suspended in toluene, solution is achieved by the addition of a small amount of tetrahydrofuran, and a solution of an appropriately substituted phenyl isocyanate (1) in toluene is added and the mixture is stirred for several hours. The resulting product (3) may be recrystallized from an appropriate solvent such as toluene, acetone, diethyl ether or ethanol. If the crude product is formed as a syrup it may be partially purified by trituration with diethyl ether and then further purified by chromatography on a silica gel column, eluting the product with 10% methanol in ethyl acetate.

The compounds of this invention inhibit thromboxane synthetase enzyme. Thus, these compounds are useful in the treatment of diseases characterized by an imbalance of thromboxane $A_2$/prostacyclin such as ischemic heart disease, transient ischemic attack, thrombosis and migraine. Recent reviews have established the role of the thromboxane/prostacyclin balance in the vascular system [*Cardiovascular Diseases: New Trends in Surgical and Medical Aspects,* H. Barnett, P. Paoletti, E. Flamm and G. Brambilla, eds., Elsevier/North-Holland Biomedical Press, pp 137–150 (1981)]. Prostacyclin ($PGI_2$) is a potent vasodilator and platelet aggregation inhibitor, whereas thromboxane ($TXA_2$) is a powerful vasoconstrictor and causative of platelet aggregation. $TXA_2$ is synthesized by thromboxane synthetase enzyme located in, for example, blood platelets. When $TXA_2$ production is increased relative to $PGI_2$, platelet aggregation, thrombosis and vasospasm may occur [Lancet (i), 1216 (1977); Lancet, 479 (1977); Science, 1135 (1976); *Amer. J. Cardiology,* 41 787 (1978)]. $TXA_2$ synthetase inhibitors have been shown to have superior anti-thrombotic action to that of aspirin [*J. Clin. Invest.,* 65, 400 (1980); *Br. J. Pharmac.,* 76, 3 (1982)].

The role of prostaglandins including $TXA_2$ and $PGI_2$ in ischemic heart patients has been reviewed [*Cardiovascular Pharmacology of the Prostagladins,* A. G. Herman, P. M. Vanhoute, H. Denolin and A. Goosens, ed., Raven Press, New York, pp 361–374 (1982)]. Injection of $TXA_2$ into coronary arteries of guinea pigs and rabbits causes myocardial ischemia and subendocardial necrosis [*Drugs of the Future,* 7 331 (1982); *Proc. Jap. Acad.,* 53(B), 38 (1977); *Eur. J. Pharmacol.,* 53 49 (1978)]. Recent research has demonstrated the beneficial effects of $PGI_2$ and selective inhibition of thromboxane synthetase on ischemic myocardium in canines [*J. Cardiovascular Pharmacology,* 4 129 (1982)]. Thus compounds which selectively inhibit thromboxane synthetase (and hence $TXA_2$) without adversely affecting $PGI_2$ are useful in the treatment of vascular diseases such as ischemia and migraine. In addition, inhibition of TXA$_2$ formation may effectively treat platelet aggregation and prevent thrombosis.

Under urethan anesthesia, 10 μl of arterial blood was collected in one ml. of 3.2% sodium citrate in a polystyrene tube from Okamoto-Aoki spontaneously hypertensive rats (SHR) (Taconic Farms, Germantown, NY) between 19 and 24 weeks in age. The blood was diluted with 3 ml. cold saline and centrifuged at room temperature for 15 minutes at 460xg. The platelet rich plasma (PRP) was separated. The platelets were isolated by centrifuging the PRP for 10 minutes at 1060xg and were washed in 4 ml. of cold oxygenated Krebs phosphate buffer, pH 7.4. The chilled platelets recovered from centrifuging at 800xg for 10 minutes were resuspended in oxygenated Krebs phosphate buffer and diluted to contain 4.5–6.0×10$^4$ platelets/μl.

The inhibition of thromboxane (TX) formation was studied by determining the concentration of thromboxane B$_2$ (TXB$_2$), the stable hydrolysis product of TXA$_2$. Assay samples, prepared on ice, contained 200 μl platelet suspension, 50 μl saline and 50 μl saline and 50 μl vehicle or drug under study. The samples were incubated for 10 minutes at 37° C. in a metabolic shaker. The reaction was terminated by immersing the tubes in an ice bath and adding 50 μl of 0.5M citric acid. The samples were centrifuged for 10 minutes in a refrigerated centrifuge and the supernatants thus obtained were decanted and stored at −20° C. The TXB$_2$ content for each sample was determined by a direct radioimmunoassay (RIA) utilizing a TXB$_2$ specific RIA kit purchased from New England Nuclear, Boston, MA and expressed as pg TXB$_2$ formed minute$^{-1}$ sample$^{-1}$, from which the percent inhibition of TXB$_2$ formation was calculated. The results of this test with representative compounds of this invention appear in Table I below.

TABLE I

| Thromboxane Synthetase Enzyme Inhibition | | |
|---|---|---|
| Compound | Dose | % Inhibition |
| N—(4-Chlorophenyl)-N'—[3-(1H—1,2,4-triazol-1-yl)Propyl]urea | $10^{-4}$ | 93 |
| N—(4-Chlorophenyl-N'—[3-(1H—imidazol-1-yl)propyl]urea | $10^{-4}$ | 92 |
| N—(3-Chlorophenyl)-N'—[3-(1H—1,2,4-triazol-1-yl)propyl]urea | $10^{-4}$ | 99 |
| N—(3-Chlorophenyl)-N'—[3-(1H—imidazol-1-yl)propyl]urea | $10^{-4}$ | 100 |
| N—(2-Chlorophenyl)-N'—[3-(1H—1,2,4-triazol-1-yl)propyl]urea | $10^{-4}$ | 86 |
| N—(2-Chlorophenyl)-N'—[3-(1H—imidazol-1-yl)propyl]urea | $10^{-4}$ | 94 |
| N—(2-Bromophenyl)-N'—[3-(1H—imidazol-1-yl)propyl]urea | $10^{-4}$ | 95 |
| N—(2-Fluorophenyl)-N'—[3-(1H—imidazol-1-yl)propyl]urea | $10^{-4}$ | 99 |
| N—(2-Fluorophenyl)-N'—[3-(1H—1,2,4-triazol-1-yl)propyl]urea | $10^{-4}$ | 70 |
| N—(2-Bromophenyl)-N'—[3-(1H—1,2,4-triazol-1-yl)propyl]urea | $10^{-4}$ | 85 |
| N—(3,4-Dichlorophenyl)-N'—[3-(1H—imidazol-1-yl)propyl]urea | $10^{-4}$ | 95 |
| N—[-(1H—1,2,4-triazol-1-yl)propyl]-N'—[3-(trifluoromethyl)phenyl]urea | $10^{-4}$ | 99 |
| N—[3-(1H—Imidazol-1-yl)propyl]-N'—phenylurea | $10^{-4}$ | 97 |
| N—(4-Bromophenyl)-N'—[3-(1H—imidazol-1-yl)propyl]urea | $10^{-4}$ | 95 |
| N—(4-Fluorophenyl)-N'—[3-(1H—imidazol-1-yl)propyl]urea | $10^{-4}$ | 100 |
| N—(4-Chlorophenyl)-N'—[5-(1H—imidazol-1-yl)pentyl]urea | $10^{-4}$ | 92 |
| N—(4-Chlorophenyl)-N'—[3-(4-methyl-1H—imidazol-1-yl)propyl]urea | $10^{-4}$ | 92 |
| N—(4-Chlorophenyl)-N'—[4-(1H—imidazol-1-yl)butyl]urea | $10^{-4}$ | 95 |
| N—[3-(1H—Imidazol-1-yl)propyl]-N'—[3-(trifluoromethyl)phenyl]urea | $10^{-4}$ | 100 |
| N—(4-Bromophenyl)-N'—[3-(1H—1,2,4-triazol-1-yl)propyl]urea | $10^{-4}$ | 86 |
| N—(4-Fluorophenyl)-N'—[3-(1H—1,2,4-triazol-1-yl)propyl]urea | $10^{-4}$ | 97 |
| N—[3-(1H—Imidazol-1-yl)propyl]-N'—(4-methoxyphenyl)urea | $10^{-4}$ | 94 |
| N—(4-Methoxyphenyl)-N'—[3-(1H—1,2,4-triazol-1-yl)propyl]urea | $10^{-4}$ | 71 |
| N—[3-(1H—Imidazol-1-yl)propyl]-N'—(4-methylphenyl)urea | $10^{-4}$ | 98 |
| N—(4-Chlorophenyl)-N'—[3-(2-phenyl-1H—imidazol-1-yl)propyl]urea | $10^{-4}$ | 86 |
| N—(4-Chlorophenyl)-N'—[4-(4-methyl-1H—imidazol-1-yl)butyl]urea | $10^{-4}$ | 100 |

Hypotensive Activity in Spontaneously Hypertensive Rats

The novel compounds of the present invention are active hypotensive agents and were tested for hypotensive activity by the method of P. S. Chan and D. Poorvin, Clinical and Experimental Hypertension, 1 (6), 817–830 (1979). Male, 16 week old, spontaneously hypertensive rats of the Okamoto strain, from Taconic Farms, Germantown, N.Y., having an average mean arterial blood pressure of 170±1.5 mm of mercury are used in the test. One to 3 rats are used per test compound. A rat is dosed by gavage with a test compound, suspended in 2% pre-boiled starch at a concentration of 50 mg./ml., at a dose of 100 mg./kg. of body weight or less, with 0.9% sodium chloride loading at a dose of 25 ml./kg. of body weight. A second identical dose of the test compound, without sodium chloride loading is given 24 hours later. At 28 hours after the initial dose the mean arterial blood pressure is measured by the method of Chan and Poorvin vide supra. The procedure is repeated in a second and third rat when necessary.

The results of this test with representative compounds of the present invention appear below in Table II.

TABLE II

| Hypotensive Activity | |
|---|---|
| Compound | Average MABP(mm Hg) (No. of Rats) |
| N—(4-Chlorophenyl)-N'—[3-(1H—1,2,4-triazol-1-yl)propyl]urea | 145 (6) |
| N—(4-Chlorophenyl)-N'—[3-(1H—imidazol-1-yl)propyl]urea | 122 (5) |
| N—(3-Chlorophenyl)-N'—[3-(1H—1,2,4-triazol-1-yl)propyl]urea | 149 (5) |
| N—(3-Chlorophenyl)-N'—[3-(1H—imidazol-1-yl)propyl]urea | 124 (3) |
| N—(2-Chlorophenyl)-N'—[3-(1H—1,2,4-triazol-1-yl)propyl]urea | 142 (2) |
| N—(2-Chlorophenyl)-N'—[3-(1H—imidazol-1-yl)propyl]urea | 123 (4) |
| N—(2-Bromophenyl)-N'—3-(1H—imidazol-1-yl)propyl]urea | 113 (2) |
| N—(2-Fluorophenyl)-N'—[3-(1H—imidazol-1-yl)propyl]urea | 135 (6) |
| N—(2-Fluorophenyl)-N'—[3-(1H—1,2,4-triazol-1-yl)propyl]urea | 149 (4) |
| N—(2-Bromophenyl)-N'—[3-(1H—1,2,4-triazol-1-yl)propyl]urea | 130 (3) |
| N—(3,4-Dichlorophenyl)-N'—[3-(1H—1,2,4-triazol-1-yl)propyl]urea | 155 (5) |

TABLE II-continued

| Hypotensive Activity | |
|---|---|
| Compound | Average MABP(mm Hg) (No. of Rats) |
| N—(3,4-Dichlorophenyl)-N'—[3-(1H—imidazol-1-yl)propyl]urea | 146 (2) |
| N—[3-(1H—1,2,4-triazol-1-yl)propyl]-N'—[3-(trifluoromethyl)phenyl]urea | 143 (2) |
| N—Phenyl-N'—[3-(1H—1,2,4-triazol-1-yl)-propl]urea | 151 (2) |
| N—[3-(1H—Imidazol-1-yl)propyl]-N'—phenyl]urea | 141 (2) |
| N—(4-Bromophenyl)-N'—[3-(1H—imidazol-1-yl)propyl]urea | 145 (2) |
| N—(4-Fluorophenyl)-N'—[3-(1H—imidazol-1-yl)propyl]urea | 134 (3) |
| N—(4-Chlorophenyl)-N'—[5-(1H—imidazol-1-yl)pentyl]urea | 153 (2) |
| N—(4-Chlorophenyl)-N'—[3-(4-methyl-1H—imidazo-1-yl)propyl]urea | 138 (3) |
| N—(4-Chlorophenyl)-N'—[4-(1H—imidazol-1-yl)butyl]urea | 131 (4) |
| N—[3-(1H—Imidazol-1-yl)propyl]-N'— | 135 (4) |
| N—(2-Chlorophenyl)-N'—[1H—imidazol-1-yl)butyl]urea | 97 (2) |
| N—(2-Bromophenyl)-N'—[4-(1H—imidazol-1-yl)butyl]urea | 98 (2) |

The novel compounds of the present invention have been found to be highly useful for inhibiting thromboxane synthetase in mammals when administered in amounts ranging from about 0.1 mg. to about 20.0 mg./kg. of body weight per day. A preferred dosage regimen for optimum results would be from about 0.5 mg. to about 10.0 mg./kg. of body weight per day. Such dosage units are employed that a total of from about 35 to about 700 mg. of active compound for a subject of about 70 kg. of body weight are administered in a 24 hour period. This dosage regimen may be adjusted to provide the optimum therapeutic response. For example, serveral divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have a molecular weight of from about 200 to 1500. Although the amount of active compound dissolved in the above vehicle may vary from 0.10% to 10.0% by weight, it is preferred that the amount of active compound employed be from about 3.0 to 9.0% by weight. Although various mixtures of the aforementioned non-volatile polethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally from about 0.05 to about 0.2% concentrations of antioxidant are employed.

For intrasmuscular injection, the preferred concentration of active compound is 0.25 to 0.50 mg./ml. of the finished compositions. The novel compounds of the present invention are equally adapted to intravenous administration when diluted with water or diluents employed in intravenous therapy such as istonic glucose in appropriate quantities. For intravenous use, intial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell gelation capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafters and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg. of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier such as fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, dye and flavoring such a cherry or orange flavor. Of course, any material used in preparing any dosate unit form should be pharmaceutically pure and substantially non-toxic in the amounts employed.

The following specific examples illustrate the preparation of the compounds of the present invention.

EXAMPLE 1

1H-Imidazole-1-propanamine

A mixture of 41 g. of imidazole and 75 ml. of acrylonitrile was heated on a steam bath for 3 hours, then concentrated under reduced pressure to remove excess acrylonitrile. A 300 ml. portion of methanol was added to the residue together with 100 ml. of concentrated ammonium hydroxide and 8 g. of Raney nickel catalyst. This mixture was hydrogenated in a Parr apparatus until hydrogen uptake ceased and then filtered giving a light green liquid. A 300 ml. portion of tetrahydrofuran was added to this liquid and the mixture filtered through diatomaceous earth. The filtrate was concentrated twice from toluene, giving 75.2 g. of the desired intermediate as a clear oil.

1H-Imidazole-1-pentanamine

A mixture of 19.6 g. of sodium imidazole 59.2 g. of N-(5-bromopentyl)phthalimide and 300 ml. of dimethylformamide as stirred in an oil bath at 100° C. for 8 hours and then concentrated to remove the dimethylformamide. The residue was extracted twice with toluene and then concentrated in vacuo, giving 51.5 g. of 2-[5-(1H-imidazol-1-yl)pentyl]-1H-isoindole-1,3(2H)-dione as an oil. This oil was mixed with 8.73 ml. of hydrazine hydrate and 400 ml. of ethanol and heated on a steam bath for 3 hours. After cooling, 360 ml. of 3N hydrochloric acid was added and the mixture was refluxed for 2 hours. This mixture was filtered and the filtrate was concentrated with intermittent filtration to about 60 ml. Potassium carbonate was added to this oil which was then extracted with dichloromethane. The extract was concentrated to an oil which was distilled (Kugelrohr), giving 13.4 g. of the desired intermediate as a clear liquid.

EXAMPLE 2

2-[4-(1H-Imidazol-1-yl)butyl]-1H-isoindole-1,3(2H)-dione

A mixture of 0.2 mol. of 2-(4-bromobutyl)-1H-isoindole-1,3(2H)-dione, 0.22 mol. of sodium imidazole and 300 ml. of dimethylformamide was stirred at 100° C. for 8 hours and then concentrated to remove the dimethylformamide. The residue was boiled with 500 ml. of toluene and the insoluble material was removed by filtration. The toluene layer was concentrated to remove the solvent and the residue was further purified by HPLC using ethyl acetate and a silica gel column. The desired product melted at 75°–77° C. Addition of ethanolic hydrogen chloride resulted in the hydrochloride salt, mp. 200°–203° C.

When the above procedure is used to react sodium imidazole with the appropriate 2-(w-bromoalkyl)-1H-isoindole-1,3(2H)-dione, the compounds of Table III were obtained.

TABLE III

| Product | m/p. °C. |
| --- | --- |
| 2-[5-(1H—imidazol-1-yl)pentyl]-1H—isoindole-1,3(2H)—dione hydrochloride | 194–197 |
| 2-[6-(1H—imidazol-1-yl)hexyl]-1H—isoindole-1,3(2H)—dione | 83–87 |
| 2-[7-(1H—imidazol-1-yl)heptyl]-1H—isoindole-1,3(2H)—dione | oil |
| 2-[8-(1H—imidazol-1-yl)octyl]-1H—isoindole-1,3(2H)—dione | 43–45 |

EXAMPLE 3

1H-Imidazole-1-butanamine

A mixture of 0.2 mole of 2-[4-(1H-imidazol-1-yl)butyl]-1H-isoindole-1,3(2H)-dione, 0.22 mol. of hydrazine hydrate and 400 ml. of ethanol was heated on the steam bath for 3 hours and then treated with 400 ml. of 3N HCl and heated at reflux for an additional 2 hours. The insoluble material was filtered off and the mother liquor was concentrated to a low volume and again filtered. The remainder of the volatile material was distilled off and the residue was treated with saturated potassium carbonate solution. The 1H-imidazole-1-butanamine was extracted into methylene chloride and further purified by distillation on a Kugelrohr apparatus. In like manner from the appropriate 2-[w-(1H-imidazol-1-yl)alkyl]-1H-isoindole-1,3(2H)-dione were prepared 1H-imidazole-1-pentanamine, 1H-imidazole-1-hexanamine, 1H-imidazole-1-heptanamine and 1H-imidazole-1-octanamine.

EXAMPLE 4

4-Methyl-1H-imidazole-1-propanamine

A mixture of 49.2 g. of 4-methyl-1H-imidazole and 75 ml. of acrylonitrile was heated on a steam bath for 6 hours and then concentrated to remove excess acrylonitrile. The residue was diluted with 400 ml. of methanol and divided into two parts. To each was added 90 ml. of ammonium hydroxide and Raney nickel catalyst. Each portion was then hydrogenated in a Parr apparatus. Each part was filtered, the filtrates combined and concentrated. The residue was concentrated from toluene. This residue was dissolved in tetrahydrofuran, stirred for one hour, filtered, concentrated, then concentrated from toluene, giving 82.2 g. of the desired intermediate as an oil.

EXAMPLE 5

2-Phenyl-1H-imidazole-1-propanamine

The procedure of Example 4 was repeated using 14.4 g. of 2-phenyl-1H-imidazole and 25 ml. of acrylonitrile, giving 18.8 g. of the desired intermediate as an oil.

EXAMPLE 6

4-Methyl-1H-imidazole-1-butanamine

The procedure of Example 2 was repeated using N-(4-bromobutyl)phthalimide and 4-methyl-1H-imidazole giving the desired intermediate. Preparation of 4-phenyl-1H-imidazole-1-propanamine, 2-methyl-1H-imidazole-1-propanamine and 2-ethyl-1H-imidazole-1-propanamine was accomplished by the procedure of Example 4 using the appropriate imidazole starting materials.

EXAMPLE 7

1H-1,2,4-Triazole-1-propanamine

The procedure of Example 1 was repeated using 55 g. of 1H-1,2,4-triazole in place of imidazole, giving 61.2 g. of the desired intermediate as an oil.

EXAMPLE 8

N-(4-Chlorophenyl)-N'-[3-(1H-imidazol-1-yl)propyl]urea

A 2.5 g. portion of 1H-imidazole-1-propanamine was added to 20 ml. of toluene and then 7 ml. of tetrahydrofuran was added to produce solution. A solution of 3.1 g. of distilled p-chlorophenyl isocyanate in 20 ml. of toluene was added, the mixture was stirred overnight and then evaporated to a waxy solid. This solid was triturated with ether and the resulting crystals recrystallized from chilled acetone, giving 2.3 g. of the desired product as colorless crystals, mp. 123°–125° C.

Following the general procedure of Example 8 and using the appropriate isocyanate derivatives the products of Examples 9–15, found in Table IV were prepared.

TABLE IV

| Example | Isocyanate | Product | MP °C. |
|---|---|---|---|
| 9 | m-chlorophenyl | N—(3-chlorophenyl)-N'—[3-(1H—imidazole-1-yl)propyl]urea | 90–97 |
| 10 | o-chlorophenyl | N—(2-chlorophenyl)-N'—[3-(1H—imidazole-1-yl)propyl]urea | 142–144 |
| 11 | o-bromophenyl | N—(2-bromophenyl)-N'—[3-(1H—imidazole-1-yl)propyl]urea | 105–106 |
| 12 | o-fluorophenyl | N—(2-fluorophenyl)-N'—[3-(1H—imidazole-1-yl)propyl]urea | 171–173 |
| 13 | 3,4-dichlorophenyl | N—(3,4-dichlorophenyl)-N'—[3-(1H—imidazole-1-yl)propyl]urea | 144–147 |
| 14 | p-bromophenyl | N—(4-bromophenyl)-N'—[3-(1H—imidazole-1-yl)propyl]urea | 112–114 |
| 15 | p-methylphenyl | N—[3-(1H—imidazole-1-yl)propyl]-N'—(4-methylphenyl)urea | 130–132 |

EXAMPLE 16

N-[3-(1H-Imidazol-1-yl)propyl]-N'-[3-(trifluoromethyl)phenyl]urea

A 2.50 g. portion of 1H-imidazole-1-propanamine was added to 20 ml. of toluene. A solution of 3.7 g. of m-trifluoromethylphenyl isocyanate in 20 ml. of toluene was added and the mixture was stirred overnight, then evaporated to a syrup. This syrup was triturated twice with ether giving 4.95 g. of crystals. These crystals were dissolved in methylene chloride, hot ethyl acetate or a mixture of the two and passed through a silica gel column, developing with 200 ml. of ethyl acetate and discarding the 200 ml. fraction. The column was then eluted with 10% methanol in ethyl acetate, collecting three 200 ml. fractions. These fractions were combined and evaporated in vacuo, giving 4.33 g. of the desired product as colorless waxy crystals, mp 105°–108° C.

Following the general procedure of Example 16 using the appropriate isocyanate derivative and 1H-imidazole-1-alkylamines and dissolving the crystals in either ethyl acetate, dichloromethane or a mixture thereof the products of Examples 17–24, found in Table V were prepared.

TABLE V

| Example | Imidazole | Isoyanate | Product | MP °C. |
|---|---|---|---|---|
| 17 | propanamine | p-fluorophenyl | N—(4-fluorophenyl)-N'—[3-(1H—imidazol-l-yl)propyl]urea | 117–118 |
| 18 | pentanamine | p-chlorophenyl | N'—(4-chlorophenyl)-N'—[5-(1H-imidazol-1-yl)pentyl]urea | 129–131 |
| 19 | 2-methyl-1H—imidazole propanamine | p-chlorophenyl | N—(4-chlorophenyl)-N'—[3-(2-methyl-1H—imidazol-1-yl)propyl]urea | |

TABLE V-continued

| Example | Imidazole | Isoyanate | Product | MP °C. |
|---|---|---|---|---|
| 20 | 4-methyl-1H—imidazole propanamine | p-chlorophenyl | N—(4-chlorophenyl)-N'—[3-(4-methyl-1H—imidazol-1-yl)-propyl]urea | 105–110 |
| 21 | 2-ethyl-1H—imidazole propanamine | p-chlorophenyl | N—(4-chlorophenyl)-N'[3-(2-ethyl-1H—imidazol-1-yl)-propyl]urea | |
| 22 | butanamine | p-chlorophenyl | N—(4-chlorophenyl)-N'—[4-(1H—imidazol-1-yl)butyl]urea | 90–92 |
| 23 | propaneamine | phenyl | N—[3-(1H—imidazol-1-yl)propyl]-N'—phenylurea | 162–163 |
| 24 | propaneamine | p-methoxyphenyl | N—[3-(1H—imidazol-1-yl)propyl]-N'—(4-methoxyphenyl)urea | 109–111.5 |
| 25 | 2-phenyl-1H—imidazole propanamine | p-chlorophenyl | N—(4-chlorophenyl)-N'—[3-(2-phenyl-1H—imidazol-1-yl)-propyl]urea | 139–141 |
| 26 | 4-phenyl-1H—imidazole propanamine | p-chlorophenyl | N—(4-chlorophenyl)-N'—[3-(4-phenyl-1H—imidazol-1-yl)-propyl]urea | |
| 27 | 4-methyl-1H—imidazole butanamine | p-chlorophenyl | N—(4-chlorophenyl)-N'—[4-(4-methyl-1H—imidazol-1-yl)-butyl]urea | 88–90 |

EXAMPLE 25

N-(2-Chlorophenyl)-N'-[4-(-1H-imidazol-1-yl)butyl]urea

A solution of 2.30 g. of o-chlorophenyl isocyanate in 30 ml. of toluene was added with stirring to a solution of 2.09 g. of 1H-imidazole-1-butanamine in 20 ml. of toluene and the mixture was allowed to stir overnight and them evaporates to a crystalline residue. The crystals were dissolved in methylene chloride and purified by HPLC (silica gel column, eluted with 10% ethanol/ethyl acetate) to obtain the desired compound, mp. 87°–88° C.

Following the general procedure of Example 25 and using the appropriate isocyanate derivative and 1H-imidazole-1-alkanamine. The products of Examples 26–29 were prepared.

TABLE VI

| Example | 1H—Imidazole | Isocyanate | Product | MP °C. |
|---|---|---|---|---|
| 26 | butanamine | m-chlorophenyl | N—(3-chlorophenyl)-N'—[4-(1H—imidazol-1-yl)-butyl]urea | oil |
| 27 | butanamine | o-bromophenyl | N—(2-bromophenyl)-N'—[4-(1H—imidazol-1-yl)-butyl]urea | 99–101 |
| 28 | hexanamine | p-chlorophenyl | N—(4-chlorophenyl)-N'—[6-(1H—imidazol-1-yl)-butyl]urea | |
| 29 | octanamine | p-chlorophenyl | N—(4-chlorophenyl)-N'—[8-(1H—imidazol-1-yl)-octyl]urea | 121–122 |

EXAMPLE 30

N-(4-Chlorophenyl)-N'-[3-(1H-1,2,4 triazol-1-yl)propyl]urea

A 1.26 g. portion of 1H-1,2,4-triazole-1-propanamine was suspended in 15 ml. of toluene and 5 ml. of tetrahydrofuran was added to produce solution. A solution of 1.55 g. of freshly distilled p-chlorophenyl isocyanate in 15 ml. of toluene was added and the mixture was stirred overnight. The resulting crystals were recrystallized from toluene, giving 2.06 g. of the desired product, mp. 137°–139° C.

Following the general procedure of this example and using appropriate isocyanate derivatives and recrystallizing from an appropriate solvent such as acetone, ether or ethanol, the products of Example 31–36 found in Table VII were prepared.

TABLE VII

| Example | Isocyanate | Product | MP °C. |
|---|---|---|---|
| 31 | m-chlorophenyl | N—(3-chlorophenyl)-N—[3-(1H—1,2,4-triazol-1-yl)propyl]-urea | 89–98 |
| 32 | o-chlorophenyl | N—(2-chlorophenyl)-N'—[3-(1H—1,2,4-triazol-1-yl)propyl]-urea | 84–90 |
| 33 | o-fluorophenyl | N—(2-fluorophenyl)-N'—[3-(1H—1,2,4-triazol-1-yl)propyl]-urea | 111–115 |
| 34 | o-bromophenyl | N—(2-bromophenyl)-N'—[3-(1H—1,2,4-triazol-1-yl)propyl]-urea | 82–90 |
| 35 | 3,4-dichlorophenyl | N—(3,4-dichlorophenyl)-N'—[3-(1H—1,2,4-triazol-1-yl)-propyl]urea | 145–148 |
| 36 | p-methylphenyl | N—(4-methylphenyl)-N'—[3-(1H—1,2,4-triazol-1-yl)propyl]-urea | 126–129 |

EXAMPLE 37

N-[3-(1H-1,2,4-triazol-1-yl)propyl]-N'-[3-(trifluoromethyl)phenyl]urea

To a solution of 2.52 g. of 1H-1,2,4-triazole-1-propanamine in 20 ml. of toluene was added a solution of 3.7 g. of m-trifluoromethhylphenyl isocyanate in 20 ml. of toluene. This mixture was stirred overnight, then evaporated to a syrup. This syrup was triturated twice with ether. The ether insoluble material was dissolved in hot ethyl acetate and applied to a silica gel column. The column was eluted with 200 ml. of ethyl acetate to remove impurities and then was developed with 10% methanol in ethyl acetate. The product fractions were combined and evaporated, giving 3.6 g. of the desired product as colorless crystals, mp. 97°–99° C.

Following the general procedure of Example 37, using appropriate isocyanate derivatives, the products of Examples 38–41, listed in Table VIII, were prepared.

TABLE VIII

| Example | Isocyanate | Product | MP °C. |
|---|---|---|---|
| 38 | phenyl | N—phenyl-N'—[3-(1H—1,2,4-triazol-1-yl)propyl]urea | 95–98 |
| 39 | p-bromophenyl | N—(4-bromophenyl)-N'—[3-(1H—1,2,4-triazol-1-yl)propyl]urea | 155–158 |
| 40 | p-fluorophenyl | N—(4-fluorophenyl)-N'—[3-(1H—1,2,4-triazol-1-yl)propyl]urea | 113–115 |
| 41 | p-methoxyphenyl | N—(4-methoxyphenyl)-N'—[3-(1H—1,2,4-triazol-1-yl)propyl]urea | 116–118 |

EXAMPLE 42

N-[3-Chlorophenyl]-N'-[2-(1H-imidazole-1-yl)ethyl]urea

The above compound, mp 93°–96° C., is obtained when m-chlorophenyl isocyanate is reacted with 1H-imidazole-1-ethanamine by the procedure of Example 8.

We claim:

1. A compound selected from the group consisting of those of the formula:

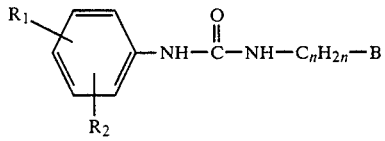

wherein $R_1$ and $R_2$ are each independently selected from the group consisting of hydrogen, fluoro, chloro, bromo, trifluoromethyl, alkyl($C_1$–$C_3$) and alkoxy($C_1$–$C_3$); n is an integer from 2 to 8, inclusive; and B is 1H-1,2,4-triazol-1-yl or a moiety of the formula:

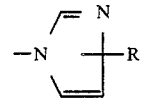

wherein R is hydrogen, alkyl($C_1$–$C_3$) or phenyl.

2. The compound according to claim 1, N-(4-chlorophenyl)-N'-[3-(1H-1,2,4-triazol-1-yl)propyl]urea.

3. The compound according to claim 1, N-(4-chlorophenyl)-N'-[3-(1H-imidazol-1-yl)propyl]urea.

4. The compound according to claim 1, N-(3-chlorophenyl)-N'-[3-(1H-imidazol-1-yl)propyl]urea.

5. The compound according to claim 1, N-(2-chlorophenyl)-N'-[3-(1H-imidazol-1-yl)propyl]urea.

6. The compound according to claim 1, N-(2-bromophenyl)-N'-[3-(1H-imidazol-1-yl)propyl]urea.

7. The compound according to claim 1, N-(2-fluorophenyl)-N'-[3-(1H-imidazol-1-yl)propyl]urea.

8. The compound according to claim 1, N-(3,4-dichlorophenyl)-N'-[3-(1H-imidazol-1-yl)propyl]urea.

9. The compound according to claim 1, N-[3-1,2,4-triazol-1-yl)propyl]-N'-[3-(trifluoromethyl)phenyl]urea.

10. N-(4-bromophenyl)-N'-[3-(1H-imidazol-yl)propyl]urea.

11. The compound according to claim 1, N-(4-fluorophenyl)-N'-[3-(1H-imidazol-1-yl)propyl]urea.

12. The compound according to claim 1, N-(4-chlorophenyl)-N'-[5-(1H-imidazol-1-yl)pentyl]urea.

13. The compound according to claim 1, N-(4-chlorophenyl)-N'-[3-(4-methyl-1H-imidazol-1-yl)propyl]urea.

14. The compound according to claim 1, N-(4-chlorophenyl)-N'-[4-(1H-imidazol-1-yl)butyl]urea.

15. The compound according to claim 1, N-[3-(1H-imidazol-1-yl)propyl]-N'-[3-(trifluoromethyl)phenyl]urea.

16. The compound according to claim 1, N-[3-(1H-imidazol-1-yl)propyl]-N'-(4-methoxyphenyl)urea.

17. The compound according to claim 1, N-[3-(1H-imidazol-1-yl)propyl]-N'-(4-methylphenyl)urea.

18. The compound according to claim 1, N-(4-chlorophenyl)-N'-[4-(4-methyl-1H-imidazol-1-yl)butyl]urea.

19. The method of inhibiting thromboxane synthetase enzyme in a mammal which comprises administering internally to said mammal a thromboxane synthetase enzyme inhibiting amount of a compound of claim 1.

20. A thromboxane synthetase enzyme inhibiting composition of matter in dosage unit form comprising from about 10 mg. to about 700 mg. of a compound of claim 1 in association with a pharmacologically acceptable carrier.

21. The method of inhibiting hypertension in a mammal which comprises administering to said mammal a hypotensive amount of a compound of claim 1.

* * * * *